United States Patent [19]

Bison et al.

[11] 4,190,592

[45] Feb. 26, 1980

[54] PROCESS FOR SPLITTING THE L-(—)-α-PHENYLETHYLAMINE SALT OF D-(—)-α-AZIDOPHENYLACETIC ACID

[75] Inventors: Günter Bison, Troisdorf-Sieglar; Reiner Elfgen, Troisdorf-Spich; Walter Heinzelmann, Lecerkusen; Josef Winterscheid, St. Augustin; Wolfgang Wolfes, Möndorf, all of Fed. Rep. of Germany

[73] Assignee: Dynamit Nobel Aktiengesellschaft, Fed. Rep. of Germany

[21] Appl. No.: 617,166

[22] Filed: Sep. 26, 1975

[30] Foreign Application Priority Data

Sep. 30, 1974 [DE] Fed. Rep. of Germany ....... 2446656

[51] Int. Cl.$^2$ .......................................... C07C 117/08
[52] U.S. Cl. .................................................. 260/349
[58] Field of Search ......................................... 260/349

[56] References Cited

U.S. PATENT DOCUMENTS 3,772,364   11/1973   Bison et al. ........................ 260/349

OTHER PUBLICATIONS

Dow Chemical Co., Dowex: Ion Exchange (1958), pp. 3, 20.

Primary Examiner—Alan L. Rotman
Assistant Examiner—Richard A. Schwartz
Attorney, Agent, or Firm—Craig and Antonelli

[57] ABSTRACT

A process for splitting the L-(—)-α-phenylethylamine salt of D-(—)-α-azidophenylacetic acid which comprises the steps of mixing the salt with a liquid diluent and an acidic cation exchange material, effecting agitation of the resulting admixture and therefore isolating a highly purified D-(—)-α-azidophenylacetic acid. This acid product is characterized by an amine content of less than 0.2% by weight.

13 Claims, No Drawings

PROCESS FOR SPLITTING THE L-(−)-α-PHENYLETHYLAMINE SALT OF D-(−)-α-AZIDOPHENYLACETIC ACID

The present invention concerns a novel process for splitting the L-(−)-α-phenylamine salt of D-(−)-α-azidophenylacetic acid wherein a particularly pure D-(−)-α-azidophenylacetic acid (APA) is obtained in a very high space-time yield.

D-(−)-α-azidophenylacetic acid serves as a valuable intermediate product for the preparation of antibiotics, such as α-azido- and α-aminobenzylpenicillin. In this procedure, the optically active substance must be present in very great purity, since only one antipode is biologically effective; whereas the other antipode or the racemate can be ineffective or even toxic. The degree of purity of optically active substances thus is frequently a decisive criterion in case these compounds are to be administered to a living organism as a nutrient or medicinal agent.

An asymmetrical syntheses of D-(−)-α-azidophenylacetic acid is unknown, so that this enantiomer is prepared by racemate separation via the diastereomeric salts. A preferred separation method practiced on a technical scale is based on the production of the salt of D-(−)-α-azidophenylacetic acid with L-(−)-α-phenylethylamine which is then cleaved by means of acids or bases—as disclosed in DOS (German Unexamined Laid-Open Application) No. 2,163,032.

The splitting of diastereomeric salts is known per se and is preferably conducted with inorganic acids or bases. In this method, special care must be taken to have the isolated D-(−)-α-azidophenylacetic acid most extensively free of phenylethylamine.

Consequently, the high requirements with respect to the purity of D-(−)-α-azidophenylacetic acid when using this conventional process make it necessary to carry out expensive extractions with aqueous hydrochloric acids of varying concentrations in order to free the D-(−)-α-azidophenylacetic acid from partially dissolved diastereomeric salt and from phenylethylamine hydrochloride. The utilization of a continuous extraction does not result in an economical process due to equilibrium adjustments. Also, temperatures of above 40° C. must be avoided in this mode of operation due to the thermal instability of D-(−)-α-azidophenylacetic acid.

It is likewise known to separate enantiomers from diastereomeric salts with the aid of ion exchange resins. However, this method is preferably carried out continuously with the aid of separating columns. Such a procedure is, however, unsuitable in the present case, because the diastereomeric salt is dissolved in a liquid phase, wherein subsequently the liberated acid would be likewise fully soluble, only to an unsatisfactory extent, unless the process is conducted with entirely uneconomically large quantities of water, from which the D-(−)-60 -azidophenylacetic acid, which is sensitive to heat and also to hydrolysis, would then have to be isolated by distilling off the water under vacuum.

Thus, there has been the problem of finding a method for cleaving the diastereomeric salt wherein the aforementioned disadvantages are avoided, the yield of D-(−)-α-azidophenylacetic acid is increased, and the extremely high purity requirements can be realized by means of a simple mode of operation.

These and other advantages are attained in accordance with the present invention by treating the L-(−)-α-phenylethylamine salt of D-(−)-α-azidophenylacetic acid in the presence of a diluent with cation exchange materials in a discontinuous process. The reaction is preferably conducted in an agitator—equipped flask or—in a particularly advantageous manner—in a forced suction filter equipped with an agitator or stirrer.

The fact that the disadvantages occurring when splitting the diastereomeric salt by repeated extraction with hydrochloric acid and/or by cleavage with cation exchangers in separating columns such as, for example, in inadequate space-time yield, can be eliminated by operating in agitator units in the presence of cation exchangers should be considered a surprising aspect of the present invention.

In the method of this invention, the D-(−)-α-azidophenylacetic acid is obtained in only a single operating step in a higher yield and with greater purity than in the heretofore conventional processes. The splitting of the diastereomeric salt in the reaction vessel by means of ion exchange resin makes it possible to operate in a suspension. Thereby, the space-time yield is substantially increased, Moreover, no waste water is produced in this method of conducting the splitting operation, since the heretofore required repeated extractions with dilute hydrochloric acid have been eliminated.

Suitable diluents are lower aliphatic alcohols and aliphatic ketones of 1 to 4 carbon atoms and the mixtures thereof with water with the mixtures containing, for example, 0.5 to 60% by weight of water. The quantity should be chosen so that 2 to 5 parts by weight, preferably 3 to 4 parts by weight of diluent are employed per one part by weight of the diastereomeric salt. Larger amounts of diluents can be used, but such use is uneconomical. The solvent mixture of acetone and water (in the preferred mixture range of 1 part by weight of water per 1 to 4 parts by weight of acetone) is preferred for technical and economical reasons, since the productivity is thereby at a maximum, expressed hereinbelow as kg. of product per cubic meter of reactor per hour. Thus, in accordance with the process of DOS No. 2,163,032, one obtains 22.6 kg. of D-(−)-APA per cubic meter per hour, while, according to the process of this invention, a productivity is attained of 66.1 kg. of D-(−)-APA per cubic meter per hour.

The diastereomeric salt need not be soluble in the diluent. The salt is then suspended in the diluent. The thus-obtained pure D-(−)-α-azidophenylacetic acid should, however, be soluble in the diluent.

The ion exchange materials employed should be acidic; such materials are known per se. In principle, all acidic cation exchange materials are suitable wherein the structure consists of inorganic compounds (zeolites, aluminum silicates) or synthetic organic compounds (e.g. phenolic resins or styrene-containing copolymers). The anchoring groups consist preferably of $SO_3$-groups. The cation exchange material can be inparticulate form, having, for example, a particle size of from 0.01 to 3.0 mm.

The reaction of the diastereomeric salts with the cation exchanger takes place by bringing these two substances into intimate contact with each other. A preferred method resides in intensively agitating the suspension of the diastereomeric salt in the diluent together with the cation exchange material.

The reaction takes place generally at room temperature. If at all possible, temperatures of above 40° C.

should be avoided due to the thermal instability of the thus-formed D-(—)-α-azidophenylacetic acid. The reaction can take place within the range of 0° C. to 40° C., preferably 15° C. to 25° C.

After splitting off the acid, the cation exchanger is separated from the liquid phase, and the latter containing the acid is worked up in accordance with conventional methods, preferably by removing the organic solvent by distillation under reduced pressure, e.g. at temperatures of from 20 to 40 at pressures of 10 to 300 ton. The thus-obtained acid is optionally recrystallized from a suitable solvent (e.g. trichloroethylene) and contains less than 0.2% of amine if the process is properly conducted.

The separated cation exchanger, which contains the phenylethylamine, is regenerated by treatment with alkalis, such as caustic soda and caustic potassium at temperatures of 10° to 30° C. for a period of 1 to 100 minutes. After thus separating the produced amine and further washing of the ion exchanger, the ion exchanger can be reused.

EXAMPLE 1 (Comparative Example)

An agitator-equipped flask having a capacity of 0.5 liter is filled with 162.4 g. of 5% by weight aqueous hydrochloric acid, 49.7 g. of the L-(—)-α-phenylethylamine salt of D-(—)-α-azidophenylacetic acid, having a rotation $[\alpha]_D^{20}$ of $-78°$ (c=5 in methanol), and 218.7 g. of trichloroethylene. The mixture is stirred at room temperature for 20 minutes; the lower trichloroethylene phase is allowed to settle and is isolated.

The aqueous phase is extracted three times with respectively 38.1 g. of trichloroethylene.

The thus-obtained trichloroethylene phases are combined and extracted three times with respectively 72.21 g. of 3% by weight aqueous hydrochloric acid and finally with 66.51 g. of desalted, i.e. demineralized, water with the addition of diaminotetraacetic acid.

After the trichloroethylene has been distilled off by a water-jet aspirator at a maximum water bath temperature of 40° C., the yield is 25,90 g. which equals 88.0% of theory of a yellow-colored oil which crystallizes after a certain period of time.

Titration with the aid of a potentiometer yielded an acid content of 98.5% by weight; the melting point was 52° to 54° C., and the index of refraction was $n_D^{20} = 1.5518$.

By perchloric acid titration, an amine content of 0.76% by weight was determined.

The rotation of D-(—)-α-azidophenylacetic acid was $[\alpha]_D^{20} = 142.3°$ (c=5 in absolute ethanol).

The thus-obtained D-(—)-α-azidophenylacetic acid is useless as an intermediate product for medicinal agents due to its high amine content of 0.76% by weight.

EXAMPLE 2

An agitator-equipped flask having a capacity of 2 liters is charged with 134.3 g. of water, 313.3 g. of acetone, and 149.2 g. of the L-(—)-α-phenylethylamine salt of D-(—)-α-azidophenylacetic acid, having a rotation $[\alpha]_D^{20}$ of $-78°$ (c=5 in absolute methanol); at 20° C., there is added to the resulting suspension 561.0 ml. of water-moistened ion exchanger on the basis of sulfonated copolymers of styrene with divinylbenzene (commercially obtainable under the name "LEWATITE" S 100, a product of Bayer, AG). Already during the addition of the ion exchanger, the initial suspension passes over into a solution. The mixture, consisting of the ion exchanger and the solution is agitated for about 1 hour at 20° C. and then the solution is separated from the ion exchanger; the latter is then washed with 198.0 g. of acetone. The acetone from the acetone water mixture is withdrawn under reduced pressure. In the thus-remaining water, the D-(—)-α-azidophenylacetic acid is separated as an oily phase and is isolated with the addition of 257 g. of trichloroethylene. Thereafter, the aqueous layer is once again extracted with 257 g. of trichloroethylene, the organic phases are combined, and the chlorinated hydrocarbon is withdrawn under 11 torr (mm.Hg) at a water bath temperature of maximally 40° C.

There remains 87.8 g. which equals 99.1% of theory, of D-(—)-α-azidophenylacetic acid, calculated on the basis of the diastereomeric salt employed.

The oily product has a refraction $n_D^{20}$ of 1.5520 and solidifies after a certain amount of time.

The crystallized substance has the following physical data:

m.p.: 52°–53° C. $[\alpha]_D^{20}$: $-143.6°$ (c=5 in absolute ethanol).

The analysis of the crystallized substance yields the following results:

(a) by conductometric titration, an acid content is determined by 99.2% by weight;
the amine content was determined
(b) by perchloric acid titration, being 0.17% by weight.

EXAMPLE 3

The cation exchanger, i.e. the resin of a sulfonated copolymer of styrene and divinylbenzene, used in the preceding example is combined in an agitator flask with 10% aqueous sodium hydroxide solution; the L-(—)-α-phenylethylamine within the cation exchanger is separated as the top or supernatant phase, and this compound is removed by evaporation. Subsequently, the sodium hydroxide solution is removed by vacuum filtering, and the exchange resin is regenerated with water, hydrochloric acid, and finally with water. The hydrochloric acid obtained from the regeneration serves for producing an aqueous L-(—)-α-phenylethylamine hydrochloride solution required for the racemate separating step. The separated sodium hydroxide solution is concentrated, the washing water is mixed with hydrochloric acid, and both solutions are utilized for the subsequent regeneration of the cation exchanger.

An agitator-equipped flask having a capacity of 2 liters is charged with the resin, regenerated according to the above-described method, and 313.3 g. of acetone as well as 134.3 g. of water are allowed to flow into the flask. Thereafter, 149.2 g. of the L-α-phenylethylamine salt of D-(—)-α-azidophenylacetic acid having a rotation $[\alpha]_D^{20}$ of $-78°$ (c=5 in absolute methanol) is added to the water-acetone mixture under agitation; this salt is already dissolved during the introduction thereof. The resulting mixture is agitated for about 30 minutes at 25° C. and then worked up in accordance with Example 2.

Yield: 88.0 g., which equals 99.3%, of theory of an oil having a slightly yellow coloring; the thus-isolated oil crystallizes after a certain period of time.

Melting point: 53°–55° C. $[\alpha]_D^{20} = -143.2°$ (c=5 in absolute $C_2H_5OH$.

The conductometric titration yielded an acid content (i.e. APA) of 99.1% by weight; the amine content, determined by perchloric acid titration, was 0.16% by weight.

EXAMPLES 4-10

By following the procedure set forth in Example 2 additional diluents and cation exchangers were used to effect splitting of L-(—)-α-phenylethylamine salt of D-(—)-α-azidophenylacetic acid and isolation of a highly purified D-(—)-α-azidophenylacetic acid.

The results of these experiments are tabulated below:

| Ex. No. | Diluent H$_2$O (gm.) | Diluent Org. Sol. (gm.) | APA Salt Amount | Ion Exch. Material Type | Ion Exch. Material Amt. (gm.) | Agitation Time (hours) | Trichloroethylene Extrations | APA Yield % | Product Analysis Acid Cont. % by wt. | Product Analysis Amine Cont. % by wt. |
|---|---|---|---|---|---|---|---|---|---|---|
| 4 | 134.3 | 313.3 | 149.2 | Lewatit S100 | 450 | 2.0 | 2 x | 99.4 | 99.3 | 0.14 |
| 5 | 134.3 | 413.0 | 149.2 | Lewatit S100 | 600 | 2.0 | 2 x | 99.7 | 99.6 | 0.10 |
| 6 | 882.0 | 378.0 | 140.0 | Lewatit S100 | 420 | 1.0 | 3 x | 99.6 | 99.5 | 0.10 |
| 7 | 110.0 | 250.0 | 149.0 | Lewatit S100 | 420 | 2.0 | 2 x | 99.5 | 99.4 | 0.13 |
| 8 | 134.3 | 313.3 | 149.2 | Lewatit S115 | 450 | 1.5 | 2 x | 99.3 | 99.4 | 0.12 |
| 9 | 134.3 | 350.0 | 149.2 | Amberlite JR124 | 450 | 1.5 | 2 x | 99.3 | 99.3 | 0.14 Styrol DVB |
| 10 | 134.3 | 350.0 | 149.2 | Amberlite XE100 | 450 | 1.5 | 2 x | 99.5 | 99.6 | 0.11 Styrol DVB |

What is claimed is:

1. A process for splitting the L-(—)-α-phenylethylamine salt of D-(—)-α-azidophenylacetic acid and for producing a pure D-(—)-α-azidophenylacetic acid, which comprises forming a suspension of the salt and a liquid diluent in which the salt is insoluble and in which D-(—)-α-azidophenylacetic acid is soluble, admixing particles of an acidic cation exchange material with said suspension, reacting the salt with the acidic cation exchange material at a temperature of not more than 40° C. in the presence of said liquid diluent and recovering a highly purified D-(—)-α-azidophenylacetic acid from the resultant reaction mixture.

2. The process according to claim 1, wherein the reaction is conducted under strong agitation in a reaction vessel.

3. The process according to claim 1, wherein 2 to 5 parts by weight of the diluent is employed per one part by weight of the salt.

4. The process according to claim 3, wherein the reaction is conducted under strong agitation in a reaction vessel.

5. The process according to claim 1, in which at least one C$_{1-4}$ alcohol or ketone, or mixtures thereof with water, are utilized as the diluent.

6. The process according to claim 5, wherein the diluent consists of a mixture of a C$_{1-4}$ alcohol or ketone and water containing from 0.5 to 60% by weight of water.

7. The process according to claim 1, wherein the salt is reacted with the cation exchange material at a temperature from 0° to 40° C.

8. The process according to claim 1, wherein the salt is reacted with the cation exchange material at a temperature of from 15° to 25° C.

9. The process according to claim 1, wherein the particles of cation exchange material have a particle size of from 0.01 to 3.0 mm.

10. A process for splitting the L-(—)-α-phenylethylamine salt of D-(—)-α-azidophenylacetic acid, which comprises mixing the salt with a liquid diluent to form a suspension of the salt and said liquid diluent, adding particles of an acidic cation exchange material to said suspension, effecting agitation of the resulting admixture, reacting the salt with the cation exchange material at a temperature of not more than 40° C. to form D-(—)-α-azidophenylacetic acid which is soluble in said diluent, separating particles of acidic cation exchange material from the resultant solutioon of said acid, and isolating a highly purified D-(—)-α-azidophenylacetic acid, characterized by an amine content of less than 0.2% by weight.

11. The process of claim 10, wherein 2 to 5 parts by weight of the diluent are employed per one part weight of the salt.

12. The process according to claim 11, wherein the particles of cation exchange material having a particle size of from 0.01 to 3.0 mm.

13. The process according to claim 12, wherein the salt is reacted with the cation exchange material at a temperature of from 0° to 40° C.

* * * * *